US006787517B1

(12) United States Patent
Gil et al.

(10) Patent No.: US 6,787,517 B1
(45) Date of Patent: Sep. 7, 2004

(54) AGENT AND METHODS FOR TREATING PAIN

(75) Inventors: Daniel W. Gil, Corona Del Mar, CA (US); Kei R. Aoki, Coto de Caza, CA (US)

(73) Assignee: Allergan, Inc., Irvine, CA (US)

(*) Notice: Subject to any disclaimer, the term of this patent is extended or adjusted under 35 U.S.C. 154(b) by 122 days.

(21) Appl. No.: 09/751,053

(22) Filed: Dec. 29, 2000

(51) Int. Cl.[7] ........................ A01N 61/00; A01N 37/18; B61K 31/00; B61K 38/00; B61K 38/28

(52) U.S. Cl. ................................. 514/1; 514/2; 514/14

(58) Field of Search .................................. 514/1, 2, 14

(56) References Cited

U.S. PATENT DOCUMENTS

| | | | | |
|---|---|---|---|---|
| 5,223,408 A | | 6/1993 | Goeddel et al. | |
| 5,595,880 A | * | 1/1997 | Weinshank et al. | 435/7.21 |
| 5,989,545 A | | 11/1999 | Foster et al. | |
| 6,641,820 B1 | | 11/2003 | Donovan | |

FOREIGN PATENT DOCUMENTS

| | | | |
|---|---|---|---|
| WO | WO95/32738 | | 12/1995 |
| WO | WO 96/01813 | * | 1/1996 |
| WO | WO96/33273 | | 10/1996 |
| WO | WO01/78702 | | 10/2001 |

OTHER PUBLICATIONS

Sawamura et al. The Journal of Neuroscience 20(24):9242–9250, Dec. 2000.*

Kolasa et al., "Alpha–1 Adrenergic Antagonist Effect on Cholinergic Muscarinic Receptors", *Society for Neuroscience Abstract*, vol. 27, No. 1, 2001, p. 1458.

* cited by examiner

*Primary Examiner*—Jezia Riley
(74) *Attorney, Agent, or Firm*—Stout, Uxa, Buyan & Mullins, LLP; Frank J. Uxa; Greg S. Hollrigel

(57) ABSTRACT

Agents for treating pain, methods for producing the agents and methods for treating pain by administration to a patient of a therapeutically effective amount of the agent are disclosed. The agent may include a clostridial neurotoxin, a fragment or a derivative thereof, attached to a targeting component, wherein the targeting component is selected from a group consisting of compounds which selectively binds at the alpha-2B or alpha-2B/alpha-2C adrenergic receptor subtype(s) as compared to other binding sites, for example, the alpha-2A adrenergic receptor subtype.

46 Claims, 1 Drawing Sheet

AGENT AND METHODS FOR TREATING PAIN

BACKGROUND OF THE INVENTION

The present invention relates to compositions and methods for treating pain. Particularly, the present invention relates to an agent comprising a neurotoxin, methods for making the agent and methods for treating pain using the agent.

"For all the happiness mankind can gain is not in pleasure, but rest from pain." John Dryden (1631–1700).

It is convenient to divide the human pain experience into two general categories, acute and chronic. Any noxious stimulus, for example extreme heat or sharp objects, may elicit an acute pain. The pain resulting from such a stimulus usually subsides in a relatively short period of time. Acute pain may also present itself in the course of any disease. However, such pain is also self-limited and subsides with time or adequate treatment.

Chronic pain is the second major category of pain experience. It can be defined as significant pain persisting for more than a few weeks for which there is no adequate therapy available to treat the underlying problem. Globally, there are countless numbers of people who presently are victims of chronic pain. For example, just in the United States alone, the National Institute of Health estimates that more than 90 million Americans suffer from chronic pain stemming from migraine headaches, back pain, arthritis, trauma, allodynia or catastrophic illness.

In general, the transduction of acute or chronic pain signals from the periphery to sensation itself is achieved by a multi-neuronal pathway and the information processing centers of the brain. The first nerve cells of the pathway involved in the transmission of sensory stimuli are called primary sensory afferents. The cell bodies for the primary sensory afferents from the head and some of the internal organs reside in various ganglia associated with the cranial nerves, particularly the trigeminal nuclei and the nucleus of the solitary tract. The cell bodies for the primary sensory afferents for the remainder of the body lie in the dorsal root ganglia of the spinal column. The primary sensory afferents and their processes have been classified histologically; the cell bodies fall into two classes: A-types are large (60–120 micrometer in diameter) while B-types are smaller (14–30 micrometer) and more numerous. Similarly the processes fall into two categories: C-fibers lack the myelin sheath that A-fibers possess. A-fibers can be further sub-divided into A beta-fibers, that are large diameters with well-developed myelin, and A delta-fibers, that are thinner with less well developed myelin. It is generally believed that A beta-fibers arise from A-type cell bodies and that A delta- and C-fibers arise from B-type cell bodies.

After the activation of the primary sensory afferents the next step in the transduction of sensory signals is the activation of the projection neurons, which carry the signal, via the spinothalamic tract, to higher parts of the central nervous system such as the thalamic nuclei. The cell bodies of these neurons (other than those related to the cranial nerves) are located in the dorsal horn of the spinal cord, This is also where the synapses between the primary afferents and the projection neurons are located. The dorsal horn is organized into a series of laminae that are stacked, with lamina I being most dorsal followed by lamina II, etc. The different classes of primary afferents make synapses in different laminae. For cutaneous primary afferents, C-fibers make synapses in laminae I and II, A delta-fibers in laminae I, II, and V, and A beta-fibers in laminae III, IV, and V. Deeper laminae (V–VII, X) are thought to be involved in the sensory pathways arriving from deeper tissues such as muscles and the viscera.

The predominant neurotransmitters at the synapses between primary afferents and projection neurons are substance P, glutamate, calcitonin-gene related peptide (CGRP) and neuropeptide Y. The efficiency of transmission of these synapses can be altered via descending pathways and by local interneurons in the spinal cord. These modulatory neurons release a number of mediators that are either inhibitory (e.g. opioid peptides, glycine, norepinephrine) or excitatory (e.g. nitric oxide, cholecystokinin, norepinephrine), to provide a mechanism for enhancing or reducing awareness of sensations.

Although the present available treatments for acute pain are usually manageable, the treatments for chronic pain are inadequate and disappointing. For example, it is known that intraspinal administration of opioids, such as morphine and fentanyl can alleviate pain. See e.g. Gianno, J., et al., *Intrathecal Drug Therapy for Spasticity and Pain*, Springer-Verlag (1996) (which publication is incorporated herein by reference in its entirety). However, these drugs used in intraspinal, or intrathecal, injections typically have only short lived antinociceptive effects. As a result, these drugs have to be frequently administered, such as by the aid of a pump for continuous infusion. For example, one frequently used pump is the SynchroMed® Infusion System, a programmable, implanted pump available from Medtronic, Inc., of Minneapolis, Minn. However, complications can arise due to the required surgical implantation procedure for the use of the pump and the known intrathecally administered drugs for pain, such as opioids, have the disadvantages of dependency and potential respiratory depression.

Longer acting analgesics are also known, for example, blocks by phenol injection. However, such treatments raise a considerable risk of irreversible functional impairment.

Botulinum Toxin

The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man and has a very potent $LD_{50}$. A specific dose of a toxin that would be lethal to 50% of the population of a certain species of animal is called an $LD_{50}$. For example, the estimated $LD_{50}$ of botulinum toxin type A (available from Allergan, Inc., of Irvine, Calif. as a purified neurotoxin complex under the trade name BOTOX®) in humans is about 150,000 picograms or about 3,000 units. Interestingly, on a molar basis, botulinum toxin type A is about 1.8 billion times more lethal than diphtheria toxin, about 600 million times more lethal than sodium cyanide, about 3.0 million times more lethal than cobra toxin and about 12 million times more lethal than cholera toxin. Singh, Critical Aspects of Bacterial Protein Toxins, pages 63–84 (chapter 4) of Natural Toxins II, edited by B. R. Singh et al., Plenum Press, New York (1996).

Seven immunologically distinct botulinum neurotoxins have been characterized, these being respectively botulinum neurotoxin serotypes A, B, $C_1$, D, E, F and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Botulinum toxin apparently binds with high affinity to cholinergic motor neurons, is translocated into the neuron and blocks the release of acetylcholine.

Without wishing to limit the invention to any theory or mechanism of operation, it is believed that the molecular mechanism of toxin intoxication appears to be similar and involve at least three steps or stages, regardless of the serotype. Although, a potential molecular mechanism of toxin intoxication of botulinum toxin is discussed here, other toxins, for example, butyricum toxins, tetani toxins or variants thereof may have the same or substantially similar mechanisms. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump, which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm of the cell.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase, which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin /B/D/F, and /G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype $C_1$ was originally thought to cleave syntaxin, but was found to cleave syntaxin and SNAP-25. Each toxin specifically cleaves a different bond (except tetanus and type B, which cleave the same bond).

Botulinum toxins have been discovered to have relatively prolonged neurotoxic effects and, as such, have been adapted for use in the treatment of pain, particularly chronic pain, for example, Foster et al. in U.S. Pat. No. 5,989,545, the disclosure of which is incorporated in its entirety herein by reference.

However, most drugs presently being used for treating pain, for example chronic pain, are still inadequate. For example, one type of chronic pain is allodynia. Allodynia is a condition wherein normal non-noxious stimuli elicit pain. Presently known compounds may partially alleviate the conditions of allodynia, but at the same time eliminate the ability of a patient to sense any pain altogether, such as acute pain caused by a noxious stimulus. The ability to detect pain resulting from a noxious stimulus is important—it allows for self-preservation. Also, many agents have undesired side effects, for example sedation, mood changes and/or hypotension. Finally, most such agents have a short therapeutic duration.

Therefore, there continues to be a need to have compounds which are selective and/or long acting for treating pain, preferably chronic pain.

SUMMARY OF THE INVENTION

In accordance with the present invention, an agent is featured comprising a therapeutic component and a targeting component, which selectively binds at either the alpha-2B or the alpha-2B and alpha-2C adrenergic receptor subtype(s) as compared to the alpha-2A adrenergic receptor subtype at the cell surface. Preferably, such cell is a neuron. In one embodiment, the agent further comprises a translocation component.

Further in accordance with the present invention, an agent according to this invention may be useful for treating pain, particularly chronic pain, in a mammal, including a human. Additionally, an agent according to this invention may be used to treat chronic pain, for example allodynia, without substantially affecting acute pain sensation or tactile sensation.

Still further in accordance with the present invention, the therapeutic component substantially interferes with the release of neurotransmitters from a cell or its processes. For example, in one embodiment, the therapeutic component comprises a light chain component, which may be able to inhibit the release of neurotransmitters from a cell. The light chain component may be a light chain or a fragment thereof of a Clostridial toxin such as a botulinum toxin type A, B, $C_1$, D, E, F, G, a butyricum toxin, a tetani toxin or variants thereof. In another embodiment, the therapeutic component may be a neurotoxin, for example saporin, through inactivating cellular ribosome functions.

Still further in accordance with the invention, the targeting components may be molecules or amino acid components. Amino acid components include, for example, peptides, polypeptides, proteins, protein complexes, and antibodies, provided that these species selectively bind at the alpha-2B or alpha-2B/alpha-2C adrenergic receptor subtype(s). In one embodiment, the molecules may be imiloxan, ARC 239, prazosin or molecules represented by the formula:

$$\text{IV}$$

[Structure IV: a pyrrole/thiophene ring with substituents R₃, R₂, R₁, X¹, bearing a -CH₂-NH-C(=S)-NH-CH₂CH₂-OH group]

wherein X' is selected from the group consisting of $R_4$—C=C—$R_5$ and $R_4$—C. A six membered carbon ring structure is formed when X' is $R_4$—C=C—$R_5$. A five membered carbon ring is formed when X' is $R_4$—C. $R_1$, $R_2$, $R_3$, $R_4$ and $R_5$ are each independently selected from the group consisting of F, Cl, Br, I, $OR_6$ and H, wherein $R_6$ is H or an alkyl, including a methyl, an ethyl or a propyl. In one embodiment, the amino acid component may be antibodies raised from an antigen component. The antigen component may include a second extracellular loop of an alpha-2B receptor, which may additionally be conjugated to a keyhole limpet hemocyanin. In one embodiment, the second extracellular loop comprises a peptide fragment comprising an amino acid sequence of KGDQGPQPRGRPQCKLNQE (SEQ ID#1). In another embodiment, the amino acid component may comprise a peptide, polypeptide, protein, protein complex or antibody, which is a variant of a wild type. For example, an amino acid component may be a mutated H chain of botulinum toxin type A which selectively binds to an alpha 2B receptor, as opposed to the wild type which has a higher affinity to motor neuron cell surface proteins. See Goeddel et al. U.S. Pat. No. 5,223,408, the disclosure of which is incorporated in its entirety herein by reference.

Still further in accordance with the present invention, the translocation component is able to facilitate the transfer of a therapeutic component, such as a light chain of a botulinum toxin type A, into the cytoplasm of the target cell. In one embodiment, the translocation component comprises a heavy chain component. The heavy chain component may include a heavy chain or a fragment thereof of a Clostridial toxin such as a botulinum toxin type A, B, $C_1$, D, E, F, G, a butyricum toxin, a tetani toxin or variants thereof. The fragment of the heavy chain may include an amino end fragment of the heavy chain. In another embodiment, the heavy chain component may comprise at least a fragment of two different neurotoxins. For example, the heavy chain component may comprise an amino end fragment of heavy chain of a botulinum toxin type A, and a carboxyl end fragment of a heavy chain of botulinum toxin type B.

Still further in accordance with the invention, the therapeutic component, the translocation component and the targeting component are joined by one or more spacer component. For example, the therapeutic component may be joined to the translocation component through a spacer component, and the therapeutic component may be joined to the targeting component through a spacer component. In one embodiment, the spacer component comprises a moiety selected from the group consisting of a hydrocarbon, a polypeptide other than an immunoglobulin hinge region, and a proline-containing polypeptide identical or analogous to an immunoglobulin hinge region. In another embodiment, the therapeutic component may be joined to the translocation component through a spacer component, and the therapeutic component may be joined to the targeting component through a disulfide bridge.

Still further in accordance with the invention, there is provided a method for making an agent of the present invention comprising the step of producing a polypeptide from a gene, which encodes for at least one component of the agent, for example the therapeutic component, the translocation component and/or the targeting component.

Still further in accordance with the invention, there is provided a method for treating pain comprising the step of administering to a mammal, preferably a human, a therapeutically effective amount of an agent of the present invention. In one embodiment, the therapeutic component and the translocation component of the agent is found together in a botulinum toxin, for example botulinum toxin type A. An agent of the present invention may be administered intrathecally or intramuscularly or subcutaneously, for example at or near the location of pain.

Still further in accordance with the invention, the agent may be employed to treat chronic pain. More preferably, the agent may be employed to treat allodynia. Even more preferably the agent may be employed to treat allodynia without substantially affecting acute pain sensation or tactile sensation. Without wishing to limit the invention to any particular theory or mechanism of operation, it is believed that the selectivity of treating allodynia without affecting acute pain or tactile sensation, as described above, is due to the agent acting selectively on alpha 2B and/or alpha 2C receptors.

DETAILED DESCRIPTION OF THE PREFERRED EMBODIMENTS

Figure 1A:
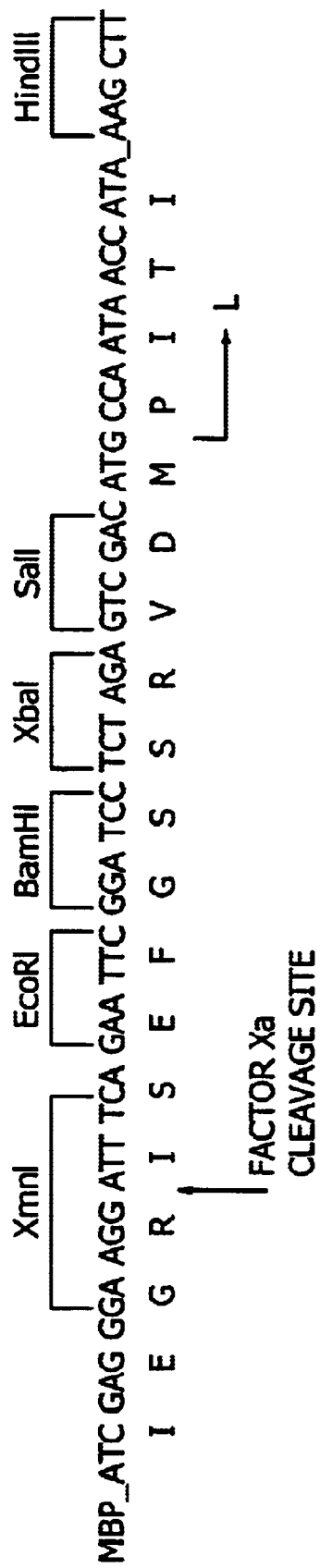
FIG. 1 is a schematic representation of the tetani toxin (hereinafter "TeTx") and the DNA construct (pMAL-L) used to express the fusion proteins comprising a light chain and a maltose binding protein, referred to herein as the MBP-L chain fusion proteins. The single letter code in the first part of the figure represents the amino acid sequence of the first several residues of the purified recombinant L chain determined by N-terminal microsequencing. The second part of the figure shows the H chain is disulfide bonded to the L chain. The location of the zinc-binding domain is also diagrammed.
Figure 1B:
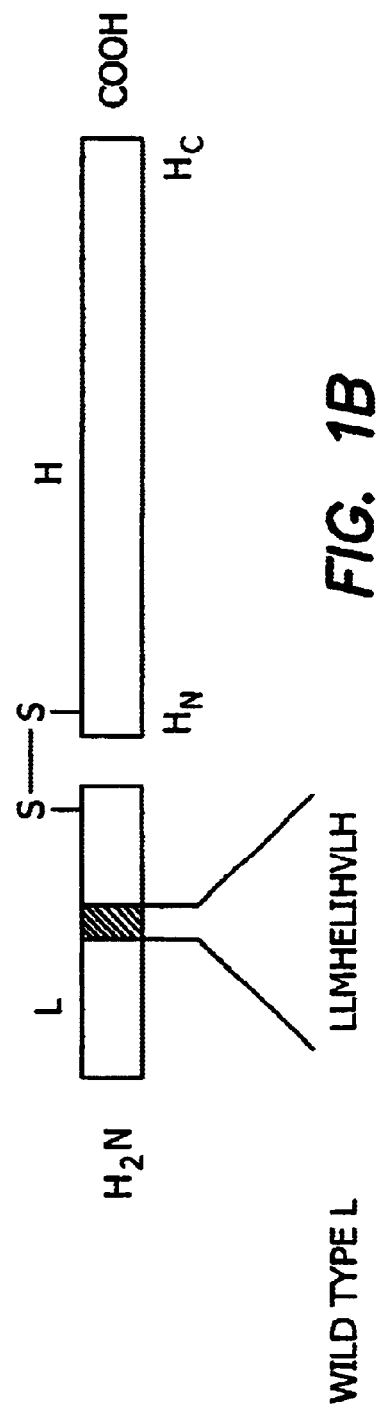

The present invention comprises agents and methods for treating pain, preferably chronic pain, such as, without limitation, allodynia and other neuropathic pain, visceral pain, pain associated with cancer and pain associated with irritable bowel syndrome.

Definitions

Light chain component comprises a light chain and/or a fragment thereof of a clostridial neurotoxin. The light chain has a molecular weight of about 50 kDa, and may be referred to as L chain or L. A light chain or a fragment thereof may have proteolytic activity.

Heavy chain component comprises a heavy chain and/or a fragment thereof of a clostridial neurotoxin. The full kDa and can be referred to as H chain or as H. The fragment of the heavy chain may be referred to as $H_C$ or $H_N$.

$H_C$ means a fragment derived from the H chain of a clostridial neurotoxin which is approximately equivalent, for example functionally equivalent, to the carboxyl end fragment of the H chain, or the portion corresponding to that fragment in the intact H chain involved in binding to cell surfaces.

$H_N$ means a fragment derived from the H chain of a clostridial neurotoxin which is approximately equivalent, for example functionally equivalent, to the amino end segment of the H chain, or the portion corresponding to that fragment in the intact in the H chain involved in the translocation of at least the L chain across an intracellular endosomal membrane into a cytoplasm of a cell.

$LH_N$ means a fragment derived from a clostridial neurotoxin that contains the L chain, or a functional fragment thereof coupled to the $H_N$ domain. It can be obtained from the intact clostridial neurotoxin by proteolysis, so as to remove or to modify the $H_C$ domain.

In a broad embodiment, an agent of this invention comprises a therapeutic component and a targeting component, which selectively binds at the alpha-2B and/or alpha-2C, preferably the alpha-2B, adrenergic receptor subtype(s) as compared to the alpha-2A adrenergic receptor subtype. In one embodiment, the targeting component is at least about 5 times more selective toward the alpha-2B and/or alpha-2C than other binding sites, for example alpha-2A receptors. In a preferred times more selective toward the alpha-2B and/or alpha-2C than other binding sites. In a more preferred times more selective toward the alpha-2B and/or alpha-2c than other binding sites. In another embodiment, the targeting component is at least about 5 times more selective toward the alpha-2B than other binding sites, for example alpha-2C receptors. In a preferred times more selective toward the alpha-2B than other binding sites. In a more preferred embodiment, the targeting component is at least about 50 times more selective toward the alpha-2B than other binding sites. The agent according to this invention is effective as a treatment for pain, preferably chronic pain.

In one embodiment, the therapeutic component substantially interferes with the release of neurotransmitters, preferably neurotransmitters which are involved in pain-signal transmissions, from a neural cell. In a preferred embodiment, the therapeutic component comprises a light chain component. The light chain component may include a light chain of a botulinum toxin, a butyricum toxin, a tetani toxin or biologically active variants of these toxins. The light chain component may also include a fragment of the mentioned light chains, providing that the fragments are biologically active in a physiological environment. That is, these fragments can substantially interfere with the release of neurotransmitters from a cell or its processes. In a preferred embodiment, the light chain component includes a light chain of a botulinum toxin type A, B, $C_1$, D, E, F, G or biologically active variants of these serotypes. In another preferred embodiment, the light chain component may even be fragments of the botulinum toxin type A, B, $C_1$, D, E, E, F, G or the biologically active variants of these serotypes, provided that the fragments themselves are biologically active, for example the fragment is able to interfere with the release of neurotoxins from a cell. As used herein, a variant polypeptide, for example a variant polypeptide, may also mean a modified polypeptide, for example modified light chain.

In another embodiment, the therapeutic component detrimentally interferes with cellular functions. For example, the therapeutic component may inactivate cellular ribosomes, preventing protein synthesis. In a preferred embodiment, the therapeutic component comprises saporin.

In yet another embodiment, the therapeutic components are neuroinhibitors. Some neuroinhibitors may interfere with the production of neurotransmitters, while other substantially prevent an action potential. Moreover, the neuroinhibitors of this invention may exert its therapeutic activity from inside a cell and/or outside a cell. Some non-limiting examples of these therapeutic components are aconitine, adenosine agonists/antagonists, adrenergics, anatoxin A, antiepileptics, baclofen, batrachotoxin, brefeldin A, brevetoxin, captopril, curare, dantrolene, doxorubicin, diazepam, grayanotoxin, lidocaine, methocarbamol, methyllycaconitine, neosaxitoxin, physostigmine, psychosine, THA, tetrodotoxin, vesamicol and vigabatum, prostaglandin receptor agonist, and antagonist. Preferably, the therapeutic component, for example, the non-limiting example above, may interfere with cells or neurons involved in the sensation of pain, preferably chronic pain.

In a broad embodiment, an agent according to this invention comprises a therapeutic component and a targeting component. In one embodiment, the therapeutic component can exert neurotoxic effects or inhibitory effects on the cell or neuron from the exterior of the cell or neuron. For example, the therapeutic component may include molecules, peptides or antibodies which prevent the release of neuronal vesicles by preventing an action potential. In one embodiment, the therapeutic component comprises an antibody, or a portion thereof. Such antibody may plug the sodium channel on the neuron's exterior to prevent the sodium influx necessary for an action potential, thus preventing the release of neurotransmitters for pain-signal transmission.

In a preferred embodiment, the therapeutic component can exert its effect from inside a cell, for example from the cytoplasm. For example, the L chain component, a therapeutic component, exerts its therapeutic effect from inside a neuron. In such a case, it is preferred that the agent further comprises a translocation component. The translocation component is able to facilitate the transfer of at least a part of the agent into the cytoplasm of the target cell. In a preferred embodiment, the translocation component comprises a heavy chain component. The heavy chain component includes a heavy chain or a fragment thereof of a botulinum toxin, a butyricum toxin, a tetani toxin or variants thereof. Preferably, the heavy chain component includes a heavy chain or a fragment thereof of a botulinum toxin type A, B, $C_1$, D, E, F, G or variants thereof. More preferably, the heavy chain component comprises a fragment of a heavy chain of a botulinum toxin type A. Even more preferably, the fragment is the amino end (or terminal) fragment of heavy chain of botulinum toxin type A which is capable of facilitating the translocation of at least part of the agent, for example the therapeutic component, from inside a vesicle into the cytoplasm of a cell.

In a preferred embodiment, an agent according to this invention comprises a therapeutic component comprising a light chain of a botulinum toxin type A and the translocation component comprising a heavy chain, preferably a fragment thereof, of a botulinum toxin type A, wherein the heavy chain (or the fragment thereof) can assist in the translocation of at least the therapeutic component into a cytoplasm of a cell. In another preferred embodiment, an agent according to this invention comprises a therapeutic component comprising a light chain of a tetani toxin and the translocation component comprising a heavy chain, preferably a fragment thereof, of a tetani toxin, wherein the fragment of a heavy chain (or the fragment thereof) can assist in the translocation of at least the therapeutic component into a cytoplasm of a cell. In yet another embodiment, an agent according to this invention comprises a therapeutic component comprising a light chain of one type of botulinum toxin and a translocation component comprising a heavy chain, preferably a fragment of the heavy chain such as the $H_N$, of another botulinum toxin, constituting a chimeric protein. For example, in one preferred embodiment, an agent in accordance with the invention comprises $LH_N$ whereof the L chain is derived from botulinum toxin type B and the amine end segment of the H chain fragment is derived from botulinum toxin type A. The $H_N$ fragment of the botulinum toxin type A is produced according to the method described by Shone C. C., Hambleton, P., and Melling, J. (1987, Eur. J. Biochem. 167, 175–180) and the L chain of botulinum. toxin type B according to the method of Sathyamoorthy, V. and DasGupta, B. R. (1985, J. Biol. Chem. 260, 10461–10466). The free cysteine on the amine end segment of the H chain fragment of botulinum toxin type A is then derivatized by the addition of a ten-fold molar excess of dipyridyl disulphide followed by incubation at 4 degree C. overnight. The excess dipvridyl disulphide and the thiopyridone by product are then removed by desalting the protein over a PD10 column (Pharmacia) into PBS. The derivatized $H_N$ is then concentrated to a protein concentration in excess of 1 mg/ml before being mixed with an equimolar portion of L chain from botulinum toxin type B (>1 mg/ml in PBS). After overnight incubation at room temperature the mixture is separated by size exclusion chromatography over Superose 6 (Pharmacia), and the fractions analyzed by SDS-PAGE. The chimeric $LH_N$ is then available for dramatization to produce a targeted conjugate.

The LH or $LH_N$ above may further be attached to a targeting component to form an agent of the present invention. The coupling of the targeting components to the therapeutic-translocation component, for example $LH_N$, is achieved via chemical coupling using reagents and techniques known to those skilled in the art. Thus, although the PDPH/EDAC and Traut's reagent chemistry may be used, any other coupling chemistry capable of covalently attaching the targeting component of the agents to the other components known to those skilled in the art is covered by the scope of this invention.

In one embodiment, the targeting components are molecules or amino acid components. The amino acid components may include, for example, peptides, polypeptides, proteins, protein complexes and antibodies or portions thereof, provided that they selectively bind at the alpha-2B or alpha-2B and alpha-2C adrenergic receptor subtype(s). These molecules, peptides or amino acid components may be agonists or antagonists of the alpha-2B or alpha-2B/alpha-2C adrenergic receptor subtype(s). In one preferred embodiment, the molecules may be imiloxan (Formula I), ARC 239 (Formula II), and prazosin (Formula III). These molecules are represented by the following general formulas:

I

Imiloxan

II

ARC 239

III

Prazosin

The molecules may also be a class of compounds represented by the general Formula IV:

IV wherein X' is selected from the group consisting of $R_4$—C=C—$R_5$ and $R_6$—C. A six membered carbon ring structure is formed when X' is $R_4$—C=C—$R_5$. A five membered carbon ring is formed when X' is $R_4$—C. $R_1$, $R_2$, $R_3$, $R_4$ and $R_5$ are each independently selected from the group consisting of F, Cl, Br, I, $OR_6$ and H, wherein $R_6$ is H or an alkyl, including a methyl, an ethyl or a propyl. In one preferred embodiment, the targeting component is a compound represented by the general Formula V:

V

In another preferred embodiment, the targeting component is a compound represented by the general Formula VI:

VI

In yet another embodiment, the targeting components are compounds (or molecules) which may be found in U.S. application Ser. No. 09/548,315, the disclosure of which is incorporated in its entirety by reference herein. These compounds or molecules include ones with the following general Formula VII, provided that the molecules have selective binding activity at the α2B or α2B/2C adrenergic receptor subtype(s) as compared to the 2A adrenergic receptor subtype:

VII

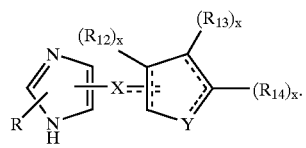

wherein the dotted lines represent optional bonds provided that two double bonds may not share a common carbon atom; R is H or lower alkyl; X is S or C(H)R$_{11}$, wherein R$_{11}$ is H or lower alkyl, but R$_{11}$ is absent when the bond between X and the ring represented by

is a double bond; Y is O, N, S, (C(R$_{11}$)$_2$)$_y$, wherein y is an integer of from 1 to 3, —CH=CH— or —Y$_1$CH$_2$—, wherein y$^1$ is O, N or S; x is an integer of 1 or 2, wherein x is 1 when R$_{12}$, R$_{13}$ or R$_{14}$ is bound to an unsaturated carbon atom and x is 2 when R$_{12}$, R$_{13}$ or R$_{14}$ is bonded to a saturated carbon atom; R$_{12}$ is H, halogen, hydroxy, lower alkyl, alkoxy, alkenyl, acyl, alkynyl, or, when attached to a saturated carbon atom, R$_{12}$ may be oxo; R$_{13}$ and R$_{14}$ are, each, H, halogen, lower alkyl, alkenyl, acyl, alkynyl, aryl, e.g. phenyl or naphthyl, heteroaryl, e.g. furyl, thienyl, or pyridyl, and substituted aryl or heteroaryl, wherein said substituent may be halogen, lower alkyl, alkoxy, alkenyl, acyl, alkynyl, nitro, cyano, trifluoromethyl, hydroxy, etc. or, together, are —(C(R$_{12}$)x)z-; —Y$_1$(C(R$_{12}$)x)z'-; —Y$_1$(C(R$_{12}$)x)y Y$_1$—; —(C(R$_{12}$)x)- Y$_1$—(C(R$_{12}$)x)-; —(C(R$_{12}$)x)-Y$_1$—(C(R$_{12}$)x)—(C(R$_{12}$)x)- and —Y$_1$—(C(R$_{12}$)x)- Y$_1$—(C(R$_{12}$)x)- wherein z is an integer of from 3 to 5, z' is an integer of from 2 to 4 and x and y are as defined above, and further either end of each of these divalent moieties may attach at either R$_3$ or R$_4$ to form a condensed ring structure shown generally as

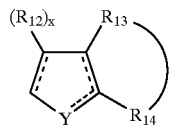

and the rings formed may be totally unsaturated, partially unsaturated, or totally saturated provided that a ring carbon has no more than 4 valences, nitrogen no more than three and O and S have no more than two. See International Patent Application No. WO 98/25669, the disclosure of which is incorporated in its entirety herein by reference.

In another embodiment, the targeting component is represented by the general Formula:

VIII

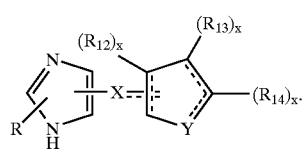

wherein X may be C(H)R$_{11}$ and R$_{11}$ is H.

Preferably, the, R$_{12}$ of Formula VIII may be H and may represent a furanyl radical.

In such furanyl derivatives of Formula II, R$_{13}$ and R$_{14}$ together may be (CH)$_4$, or R$_{13}$ may be H and R$_{14}$, may be t-butyl, or R$_{13}$ and R$_{14}$, may be H, or R$_{13}$ may be H and R$_{14}$ may be methyl or ethyl.

Alternatively, in Formula VIII, R$_{11}$ may be methyl and

may represent a furanyl radical.

Alternatively, in said compounds of Formula VIII, R$_{12}$ may be H and

may represent a thienyl radical.

In such thienyl derivatives of Formula II, R$_{13}$ and R$_{14}$, together, may represent (CH$_2$)$_4$, or R$_{13}$ may be phenyl and R$_{14}$ may be H, or R$_{13}$ and R$_{14}$, together, may represent (CH$_2$)$_3$S, or R$_{13}$ and R$_{14}$ may be H, or R$_{13}$ and R$_{14}$, together, may represent (CH)$_4$, or may be R$_{13}$ may be H and R$_{14}$ may be methyl, or R$_{13}$ may be bromo and R$_{14}$ may be H, or R$_{13}$ may be hydrogen and R$_{14}$ may be chloro, or R$_{13}$ may be methyl and R$_{14}$ may be hydrogen.

Alternatively, in the compounds of Formula VIII

may represent a cyclohexyl radical.

In such cyclohexyl derivatives of formula VIII, R$_{12}$ may be hydrogen and R$_{13}$ and R$_{14}$ may, together, represent (CH)$_4$, or R$_{12}$ may be oxo and R$_{13}$ and R$_{14}$, together, may be (CH)$_4$, or R$_{12}$ may be hydrogen or oxo and R$_{13}$ and R$_{14}$, together, may represent (CH)$_2$S, or R$_{12}$ may be hydrogen and R$_{13}$ and R$_{14}$ may, together, represent (CH$_2$)$_4$, forming an octahydronaphthalene, or R$_{12}$ may be oxo and R$_{13}$ and R$_{14}$ may, together, represent (CH$_2$)$_4$, or R$_{12}$ may be oxo and R$_{13}$ and R$_{14}$, together, may represent (CH)$_2$ C(CH$_3$) (CH), or R$_{12}$ may be hydrogen and R$_{13}$ and R$_{14}$, together, may represent S(CH$_2$)$_{21}$ or R$_{12}$, R$_{13}$ and R$_{14}$, may be H, or R$_{12}$ may be oxo and R$_{13}$ and R$_{14}$ together may represent —Y$_1$—C(R$_2$)$_x$—C(R$_2$)$_x$—Y$_1$— wherein Y$_1$ is N, forming a tetrahydroquinoxaline wherein R$_{12}$ may be hydrogen or oxo.

Alternatively, in the compounds of Formula VIII

may represent a tetrahydroquinoline radical wherein R$_{13}$ and R$_{14}$ together are —Y$_1$—C(R$_2$)$_x$—C(R$_2$)$_x$—C(R$_2$)$_x$— wherein Y$_1$ is N. In such tetrahydroquinoline derivatives $(R_{12})_x$ may be hydrogen or oxo; or may represent a tetrahydro-isoquinoline radical wherein $R_{13}$ and $R_{14}$ together are —$C(R_2)_x$—$Y_1$—$C(R_2)_x$—$C(R_2)_x$— wherein $Y_1$ is N and $(R_{12})_x$ may be hydrogen or oxo Alternatively, in the compounds of Formula VIII

may represent a cyclopentyl radical.

In such cyclopentyl derivatives of formula VIII, $R_{12}$ may be H and $R_{13}$ and $R_{14}$, together, may represent $(CH)_4$, or $R_{12}$ may be oxo and $R_{13}$ and $R_{14}$, together, may represent $(CH)_4$, or $R_{12}$ may be hydrogen and $R_{13}$ and $R_{14}$, together, may represent $(CH_2)_3$.

In another aspect of the invention, Y is $(CH_2)_3$ and X may be CH and $R_{12}$ may be oxo or X may be $CH_2$ and $R_{12}$ may be H and $R_{13}$ and $R_{14}$, together, may represent $(CH)_4$. Alternatively, $R_{13}$ and $R_{14}$, together, may represent $(CH)_4$, Y may be $CH_2C(C(R_{11})_2)_2$ wherein $R_{11}$ is hydrogen, or Y may be —$CH_2C(Me)$— and $R_{12}$ may be hydrogen or oxo.

Finally, in the compounds of Formula VIII

may represent a phenyl radical.

In such phenyl derivatives of Formula VII, X may be $CH_2$, R maybe H or $CH_3$, $R_{12}$, $R_{13}$ and $R_{14}$ may be H, or $R_{13}$ and $R_{14}$, together, represent $O(CR_2)_2O$ to provide a 1,4-benzodioxan derivative, or alternatively, X may be S and $R_{12}$, $R_{13}$ and $R_{14}$, may be H.

In another aspect of the invention, said compound has the general Formula IX:

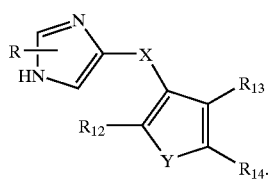

wherein Y is S or O.

In such compound of Formula III, X may be $C(H)R_{11}$, R, $R_1$, $R_2$, $R_{13}$ and $R_{14}$ may be H and Y may be O or S.

In another aspect of the invention, said compound has the formula X.

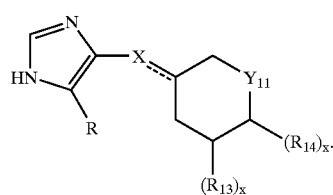

and $R_{13}$ and $R_{14}$, together, represent $(CH)_4$.

In such compounds of Formula X, $Y_1$ may be O, $R_{12}$ may be oxo and X is CH or $CH_2$, or one of $R_{12}$ is hydroxy and the other may be H, or $R_{12}$ may be H.

In such compounds of Formula IV, $Y_1$ may be S, X may be $CH_2$ and $R_{12}$ may be oxo, or $R_{12}$ may be H and X may be CH and $R_{12}$ may be oxo.

In another aspect of the invention, the compound having selective binding activity at the 2B or 2B and 2C adrenergic receptor subtype(s) as compared to the 2A adrenergic receptor subtype is represented by the formula XI.

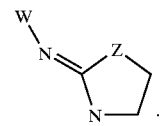

wherein W is a bicyclic radical selected from the group consisting of

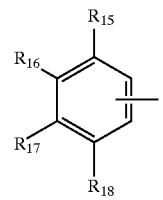

wherein $R_{15}$, $R_{16}$, $R_{17}$ and $R_{18}$ are selected from the group consisting of H and lower alkyl provided that at least one of $R_{15}$ and $R_{16}$ or $R_{16}$ and $R_{17}$ are $OC(R_{19})C(R_{19})N(R)$ to form a condensed ring with

wherein $R_{19}$ is H, lower alkyl or oxo; and

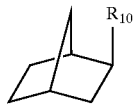

wherein $R_{20}$ is H, lower alkyl, phenyl or lower alkyl substituted phenyl, and Z is O or NH. Compounds wherein W is norbornyl are disclosed and claimed in commonly assigned co-pending application Ser. No. 09/003902, filed on 7 Jan., 1998, which is hereby incorporated by reference in its entirety.

In one aspect of the invention Z may be O and W may be

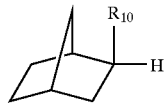

and $R_{20}$ may be selected from the group consisting of H, phenyl and o-methylphenyl, e.g. $R_{20}$ may be o-methylphenyl.

In another aspect of the invention W may be

[chemical structure with $R_{15}$, $(R_{19})_x C$, O, N, R]

wherein Z may be NR, R may be methyl or hydrogen, one of $(R_{19})_x$ may be H and $R_{15}$ may be H.

Alternatively, W may be

[chemical structure with O, N, R, $R_{18}$]

wherein R may be H and $R_{18}$ may be methyl.

It is understood that wherein a reference to lower alkyl, alkoxy, alkenyl or alkynyl is made above, it is intended to mean radicals having from one to eight carbons, preferably from one to four carbon atoms. Where reference to aryl is made above, it is intended to mean radicals of from six to fourteen carbon atoms, preferably from six to ten carbon atoms. Where reference is made to halogen, fluoro and chloro are preferred.

In one embodiment, the targeting component may be an amino acid component. An amino acid component may be a peptide, a polypeptide, a protein, a protein complex, an antibody or a portion thereof. Preferably the amino acid component is a protein, more preferably an antibody, even more preferably a portion of an antibody, which selectively binds to the alpha-2B and/or the alpha-2C receptor. In one embodiment, a portion of an antibody may be a Fab portion. In one embodiment the amino acid component may be an antibody. The antibody may be raised from an antigen component. The antigen component may include an extracellular loop of an alpha-2B or C receptor, which may additionally be conjugated to a keyhole limpet hemocyanin. In one embodiment, the extracellular loop comprises a peptide fragment comprising an amino acid sequence of KGDQGPQPRGRPQCKLNQE (SEQ ID#1).

In another embodiment, the amino acid component comprises a variant peptide, polypeptide, protein, protein complex, antibody or a portion thereof of a corresponding wild type. For example, a naturally existing heavy chain of a botulinum toxin is a wild type polypeptide. Preferably, the targeting component comprising a variant of a wild type is able to selectively bind to alpha-2B and/or C receptor and is free of at least one undesired binding property of the wild type sequence of amino acid. For example, in one embodiment, the targeting component comprising a variant of a wild type selectively binds to alpha-2B and/or C receptor and does not bind to a motor neuron cell surface.

In one embodiment, there is one targeting component per agent of the present invention. In another embodiment, there are more than one targeting components per agent of the present invention. For example, an agent comprising a therapeutic component, such as a light chain, may further include a peptide fragment attached to the light chain, wherein one or more targeting components may be attached.

A single agent of the present invention may comprise any number of targeting components, as long as the added targeting component enhances the agent's effectiveness, for example, allow the agent to bind to the −2B and/or C more selectively and/or with higher affinity. In one embodiment, a single agent comprises two targeting components. In another embodiment, a single agent comprises three targeting components.

Methods for producing variants of wild type are known. For example, Goeddel et al. in U.S. Pat. No. 5,223,408 disclose a method for producing variant proteins which retains at least one desired binding property and eliminating at least one undesired binding property of the wild type protein. The disclosure of Goeddel et al. is incorporated in its entirety herein by reference. In general, the method of Goeddel et al. comprises (a) obtaining at least a first and second reporter molecule capable of binding to different epitopes on the selected wild-type protein; (b) mutating DNA encoding the selected wild-type protein thereby creating a library of related variant DNA molecules; (c) inserting each DNA molecule created in step (b) into an expression vector, wherein the vector comprises DNA encoding a transmembrane anchor domain thereby creating a library of vectors; (d) transfecting eukaryotic cells, preferably mammalian, with the vectors of step (c); (e) culturing the cells of step (d) under conditions inducing the expression of the DNA to produce a chimeric fusion protein immobilized on the cell membrane; (f) contacting the cultured cells of step (e) with the first and second reporter molecules under conditions for which at least a portion of the cultured cells bind to the first or second reporter molecules; (g) sorting the contacted cells, preferably by fluoresence activated cell sorting (FACS), based on a desired binding pattern with the first or second reporter molecules; and (h) obtaining the variant proteins having the desired binding pattern from the sorted cells from (g). The preferred binding pattern comprises binding the cells with the first reporter molecule and the absence of binding of the cells with the second reporter molecule.

The first and second reporter molecules generally comprise a detectable marker conjugated to a molecule selected from; antibodies, ligands, and soluble receptors that are capable of binding with the wild-type protein. The first and second reporter molecules are typically monoclonal antibodies (Mabs) each conjugated to a different fluorophore. Normally the fluorophores will be fluorescein or phycoerythrin.

In one embodiment, the components of the agents are joined by a spacer component. Spacer components have many functions within this invention. For example, one of the functions of the spacer regions is to provide for adequate distance between the various components so that the components can independently and freely move about, without substantial internal steric hindrance. Such a spacer may comprise, for example, a portion of the botulinum toxin $H_C$ sequence (preferably the portion does not retain the ability to bind to motor neurons or sensory afferent neurons), another sequence of amino acids, or a hydrocarbon moiety. The spacer component may also comprise a proline, serine, threonine and/or cysteine-rich amino acid sequence similar or identical to a human immunoglobulin hinge region. In a preferred embodiment, the spacer region comprises the amino acid sequence of an immunoglobulin $\Delta_1$ hinge region; such a sequence has the sequence (from N terminus to C terminus):EPKSCDKTHTCPPCP (SEQ ID#2). In one embodiment, the therapeutic component attaches to the translocation component through a spacer component, and the translocation component also attaches to the targeting component through a spacer component. In a preferred embodiment, the therapeutic component attaches to the translocation component through a spacer component, and the therapeutic component also attaches to the targeting component through a spacer component, or alternatively a disulfide bond. In a more preferred embodiment, the therapeutic component is a light chain of a botulinum toxin type A, the translocation component is a heavy chain, or a fragment thereof, of a botulinum toxin type A which can facilitate the translocation of at least the light chain into a cytoplasm of a cell, and the targeting component is a molecule which can selectively bind to the alpha-2B and/or C receptors. For example, such a selectively binding molecule may be an agonist or antagonist of the alpha-2B and/or C receptor. An example of such molecule may be represented by the formula:

$$\begin{array}{c} R_3 \underset{R_2}{\overset{X^1}{\underset{R_1}{\longrightarrow}}} \underset{H}{\overset{S}{\underset{H}{\longrightarrow}}} N \underset{H}{\overset{S}{\underset{H}{\longrightarrow}}} OH. \end{array} \quad IV$$

wherein X' is selected from the group consisting of $R_4$—C=C—$R_5$ and $R_4$—C. A six membered carbon ring structure is formed when X' is $R_4$—C=C—$R_5$. A five membered carbon ring is formed when X' is $R_4$—C. $R_1$, $R_2$, $R_3$, $R_4$ and $R_5$ are each independently selected from the group consisting of F, Cl, Br, I, $OR_6$ and H, wherein $R_6$ is H or an alkyl, including a methyl, an ethyl or a propyl.

In one embodiment, the therapeutic component and the translocation component are part of a botulinum toxin, for example botulinum toxin type A. In such a case, a natural, a chemically modified, a recombinant or partially recombinant botulinum toxin type A may be attached to a targeting component, forming the agent of the present invention. Furthermore, it is known in the art that the $H_c$ of the neurotoxin molecule, for example botulinum toxin type A, can be removed from the other segment of the H chain, the $H_N$, such that the $H_N$ fragment remains disulphide linked to the L chain of the neurotoxin molecule to provide a fragment known as known as the $LH_N$. Thus, in one embodiment of the present invention the $LH_N$ fragment of a Clostridial neurotoxin, for example botulinum toxin type A, is covalently coupled, using a spacer component to a targeting component forming an agent of the present invention. In another embodiment of the invention, the $H_c$ part of the Clostridial neurotoxin, for example botulinum toxin type A, may be mutated or modified, e.g. by chemical modification, to reduce, or preferably incapacitate, its ability to bind the neurotoxin to receptors at the neuromuscular junction. This modified Clostridial neurotoxin, for example botulinum toxin type A, is then covalently coupled, using one or more spacer components, to a targeting component forming an agent of the present invention. In one embodiment, a linker may be employed to join various components together. For example, a linker may be used to join a spacer component to a therapeutic component. Additionally, a linker may be used to join a therapeutic component with a targeting component. Various non-limiting embodiments which include the use of linkers are provided in the examples below.

According to another broad aspect of this invention recombinant techniques are used to produce at least one of the components of the agents. See, for example the disclosure of which is incorporated in its entirety herein by reference. The technique includes steps of obtaining genetic materials from DNA cloned from natural sources, or synthetic oligonucleotide sequences, which have codes for one of the components, for example the therapeutic, translocation and/or targeting component(s). The genetic constructs are incorporated into host cells for amplification by first fusing the genetic constructs with a cloning vectors, such as phages or plasmids. Then the cloning vectors are inserted into hosts, preferably E. coli's. Following the expressions of the recombinant genes in host cells, the resultant proteins can be isolated using conventional techniques. The protein expressed may comprise all three components of the agent. For example, the protein expressed may include a light chain of botulinum toxin type A (the therapeutic component), a heavy chain, preferably the $H_N$, of a botulinum toxin type A (the translocation component), and a Fab portion of an antibody which selectively binds to an alpha-2B adrenergic receptor under physiological conditions. In one embodiment, the protein expressed may include less than all three components of the agent. In such case, the components may be chemically joined, preferably through a spacer region.

There are many advantages to producing these agents recombinantly. For example, production of neurotoxin from anaerobic clostridium cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous Clostridial proteases through a process termed nicking. This involves the removal of approximately 10 amino acid residues from the single-chain to create the dichain form in which the two chains remain covalently linked through the intrachain disulfide bond.

The nicked neurotoxin is more active than the unnicked form. The amount and precise location of nicking varies with the serotypes of the bacteria producing the toxin or with the modification made in the outer loop. The differences in single-chain neurotoxin activation and, hence, the yield of nicked toxin, are due to variations in the type and amounts of proteolytic 1 Is activity produced by a given strain. For example, greater than 99% of *Clostridial botulinum* type A single-chain neurotoxin is activated by the Hall A *Clostridial botulinum* strain, whereas type B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered Clostridial toxins is, therefore, an important consideration for manufacture of these materials. It would be a major advantage if neurotoxins such as botulinum toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and L chains of tetanus and botulinum toxins; these isolated chains are, by themselves, non-toxic; see Li et al., *Biochemistry* 33:7014–7020 (1994); Zhou et al., *Bio-*

*chemistry* 34:15175–15181 (1995), hereby incorporated by reference herein. Following the separate production of these peptide chains and under strictly controlled conditions the H and L subunits can be combined by oxidative disulphide linkage to form the neuroparalytic di-chains.

In one embodiment, an agent comprising a therapeutic component and a translocation component is recombinantly produced as an unnicked single chain. See Dolly et al. U.S. Pat. No. 09/648,692, the disclosure of which is incorporated in its entirety by reference herein. In a preferred embodiment, the agent includes an amino acid sequence that is susceptible to specific cleavage in vitro following expression as a single chain. Such proteins may include clostridial neurotoxins and derivatives thereof, such as those proteins disclosed in U.S. Pat. No. 5,989,545 and International Patent Application WO95/32738, both incorporated by reference herein.

In one embodiment of the invention the protein comprises the functional domains of a clostridial neurotoxin H chain and some or all of the functions of a clostridial neurotoxin L chain in a single polypeptide chain, and having an inserted proteolytic cleavage site located between the H domain and the L domain by which the single chain protein may be cleaved to produce the individual chains, preferably covalently linked by a disulfide linkage. The proteolytic cleavage sites comprise amino acid sequences that are selectively recognized and cleaved by a specific enzyme.

In a preferred embodiment of the invention, the expressed single-chain proteins comprise the biologically active domains of the H chain and L chain of a clostridial neurotoxin. Scission at the internal proteolytic cleavage site separating the chain domains thus results in the activation of a neurotoxin having full activity.

In another embodiment of the invention the single-chain proteins comprise a targeting component targeted to a cell receptor other than one borne by a motor neuron. Such a binding domain may specific bind to, for example, an alpha-2B and/or adrenergic receptor. The single-chain proteins will contain a translocation component similar to that of clostridial neurotoxins, and a therapeutic component. The therapeutic component may be a clostridial neurotoxin light chain, or may be a different therapeutic component such as an enzyme, a transcribable nucleotide sequence, growth factor, an antisense nucleotide sequence and the like.

Preferably, the toxins and toxin-based proteins of the present invention will be tailored to contain an additional amino acid sequence comprising a binding tag able to bind a target compound at sufficiently high efficiency to facilitate rapid isolation of the toxin protein. Proteins containing such binding sites are many and well known to those of skill in the art, and may comprise, without limitation, monoclonal antibodies, maltose binding protein, glutathione-S-transferase, protein A, a $His_6$ tag, and the like.

To minimize the safety risk associated with handling neurotoxin, the agents, or toxins of the this aspect of the present invention are expressed as their low activity (or inactive) single-chain proforms, then, by a carefully controlled proteolytic reaction in vitro, they are activated, preferably to the same potency level as the native neurotoxin from which they were derived. To improve the efficiency and rate of proteolytic cleavage the engineered proteolytic cleavage sites can be designed to occur in a specially-designed loop between the H and L portions of the single amino acid chain that promotes accessibility of the protease to the holotoxin substrate.

To reduce the risk of unintentional activation of the toxin by human or commonly encountered proteases, the amino acid sequences of the cleavage site are preferably designed to have a high degree of specificity to proteolytic enzymes which do not normally occur in humans (as either human proteases or occurring in part of the foreseeable human fauna and flora). A non-exclusive list of examples of such proteases includes bovine enterokinase, which cleaves the amino acid sequence DDDDK; tobacco etch virus (TEV) protease, which cleaves the sequence EXXYXQS/G; GENENASE® from *Bacillus amyliquifaciens*, which cleaves the sequence HY or YH; and PRESCISSION® protease from human rhinovirus 3C, which cleaves the amino acid sequence LEVLFQGP. As used above, the letter X indicates any amino acid. All amino acid sequences shown in the present specification are in the direction from amino terminus to carboxyl terminus, and all nucleotide sequences from 5' to 3', (from left to right) unless otherwise indicated.

In another aspect of the invention the interchain loop region of the *C. botulinum* subtype E neurotoxin, which is normally resistant to proteolytic nicking in the bacterium and mammals, is modified to include the inserted proteolytic cleavage site, and this loop region used as the interchain loop region in the single-chain toxin or modified toxin molecules of the present invention. It is believed that using the loop from *C. botulinum* subtype E will stabilize the unnicked toxin molecule in vivo, making it resistant to undesired cleavage until activated through the use of the selected protease.

In a broad embodiment, an agent according to this invention may be used to treat pain in a mammal, preferably a human. The agents described in this invention can be used in vivo, either directly formulated or as a pharmaceutically acceptable salt, for treatment of pain. Preferably, the agent may be employed to treat chronic pain. More preferably, the agent may be employed to treat allodynia. Even more preferably the agent may be employed to treat allodynia without substantially affecting acute pain sensation or tactile sensation. Without wishing to limit the invention to any particular theory or mechanism of operation, it is believed that the selectivity of treating allodynia without affecting acute pain or tactile sensation, as described above, is due to the agent acting selectively on alpha 2B and /or alpha 2C receptors.

In one embodiment, a method for treating pain comprises the step of administering to a mammal, preferably a human, a therapeutically effective amount of an agent according to this invention. Various non-limiting examples of the types of pain which may be treated in accordance with this invention are chronic pain, allodynic pain, visceral pain, neuropathic pain and referred pain. In a preferred embodiment, the agent to be administered includes a therapeutic component which comprises a light chain of botulinum toxin type A, a translocation component which comprises a fragment of the heavy chain of botulinum toxin type A which is able to facilitate the transfer of at least the light chain into the cytoplasm of the target cell, and a targeting component which is represented by the general Formula IV:

IV $$R_3 - \underset{R_2 \quad R_1}{\underset{\|}{X^1}} - CH_2 - \underset{H}{N} - \underset{\|}{\overset{S}{C}} - \underset{H}{N} - CH_2CH_2 - OH.$$

wherein X' is selected from the group consisting of $R_4-C=C-R_5$ and $R_4-C$. A six membered carbon ring structure is formed when X is $R_4$—C=C—$R_5$. A five membered carbon ring is formed when X' is $R_4$—C. $R_1$, $R_2$, $R_3$, $R_4$ and $R_5$ are each independently selected from the group consisting of F, Cl, Br, I, $OR_6$ and H, wherein $R_6$ is H or an alkyl, including a-methyl, an ethyl or a propyl.

The dose of the agent to be administered depends on many factors. For example, the better each one of the components is able to perform its respective function, the lower the dose of the agent is required to obtain a desired therapeutic effect. One of ordinary skill will be able to readily determine the specific dose for each specific agent. For agents employing a natural, mutated or recombinant botulinum toxin a the therapeutic and translocation component, an effective dose of an agent to be administered may be about 1 U to about 500 U of the botulinum toxin. In a preferred embodiment, the administered agent comprises about 10 U to about 300 U of the botulinum toxin.

In one embodiment, the routes of administration of the present invention include, but are not limited to, transdermal, parenteral, subcutaneous, intramuscular, intravenous, intrarectal and intraspinal administrations. As used herein nintraspinalo means into or within the epidural space, the intrathecal space, the white or gray matter of the spinal cord or affiliated structures such as the dorsal root and dorsal root ganglia. Preferably, the intraspinal administration is carried out intrathecally because of the greater ease in which the relatively larger intrathecal space is accessed and because the preferred agents generally exhibits low solubility in the lipid rich epidural environment. Additionally, intraspinal administration of the agents according to the present invention can be by various routes such as by catheterization or by spinal tap injection. The long lasting nature of the therapeutic effects of the present invention substantially removes the need for chronic antinociceptive drug administration, so that the present methods are advantageously practiced by infrequent spinal tap injection of the agents. Furthermore, an intrathecal spinal tap agents administration route facilitates a more precise and localized delivery of agents with less danger of damage to the CNS, as compared to moving a catheter to access other CNS locations. For example, the agent may be administered intrathecally to the cranial region, the cervical region, the thoracic region, the lumbar region and/or the sacral region of the central nervous system. After the administration of the agent, the alleviation of pain, preferably chronic pain, more preferably allodynia type pain, persists from about 2 to about 27 months. Even more preferably, the allodynia type pain is alleviated without substantially affecting acute pain sensation or tactile sensation.

An intraspinal route for administration of an agent according to the present disclosed invention can be selected based upon criteria such as the solubility characteristics of the agents chosen as well as the amount of the agents to be administered. The amount of the agents administered can vary widely according to the particular disorder being treated, its severity and other various patient variables including size, weight, age, and responsiveness to therapy. For example, the extent of the area of CNS afferent pain neuron somata influenced is believed to be proportional to the volume of agents injected, while the quantity of the analgesia is, for most dose ranges, believed to be proportional to the concentration of agents injected. Furthermore, the particular intraspinal location for administration of an agent may depend upon the dermosome location of the pain to be treated. Methods for determining the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14$^{th}$ edition, published by McGraw Hill).

The following examples illustrate how a therapeutic component, for example a light chain of a Clostridial toxin, may be recombinantly produced and reassociated with a translocation component, for example a heavy chain of a Clostridial toxin. The examples also illustrate how the various components of an agent according to this invention may be joined together.

EXAMPLE 1

Subcloning the BoNT/A-L Chain Gene

Example 1 describes the methods to clone the polynucleotide sequence encoding the BoNT/A-L chain. The DNA sequence encoding the BoNT/A-L chain may be amplified by a PCR protocol that employs synthetic oligonucleotides having the sequences, 5'-AAAGGCCTTTTGTT AATAAACAA-3' (SEQ ID#3) and 5'-GGAATTCTTAC TTATTGTATCCTTTA-3' (SEQ ID#4). Use of these primers allows the introduction of Stu I and EcoR I restriction sites into the 5' and 3' ends of the BoNT/A-L chain gene fragment, respectively. These restriction sites may be subsequently used to facilitate unidirectional subcloning of the amplification products. Additionally, these primers introduce a stop codon at the C-terminus of the L chain coding sequence. Chromosomal DNA from C. botulinum (strain 63 A) may serve as a template in the amplification reaction.

The PCR amplification is performed in a 1001 µl volume containing 10 mM Tris-HCI (pH 8.3), 50 mM KCI, 1.5 mM $MgCI_2$, 0.2 mM of each deoxynucleotide triphosphate (dNTP), 50 pmol of each primer, 200 ng of genomic DNA and 2.5 units of Taq-polymerase (Promega). The reaction minute at 94° C.), annealing (2 minutes at 37° C.) and polymerization (2 minutes at 72° C.). Finally, the reaction is extended for an additional 5 minutes at 72° C.

The PCR amplification product may be digested with Stu I and EcoR I, purified by agarose gel electrophoresis, and ligated into Sma I and EcoR I digested pBluescript II SK* to yield the plasmid, pSAL. Bacterial transformants harboring this plasmid may be isolated by standard procedures. The identity of the cloned L chain polynucleotide is confirmed by double stranded plasmid sequencing using SEQUENASE (United States Biochemicals) according to the manufacturer's instructions. Synthetic oligonucleotide sequencing primers are prepared as necessary to achieve overlapping sequencing runs. The cloned sequence is found to be identical to the sequence disclosed by Binz, et al., in J. Biol. Chem. 265:9153 (1990), and Thompson et al., in Eur. J. Biochem. 189:73 (1990).

Site-directed mutants designed to compromise the enzymatic activity of the BoNT/A-L chain may also be created.

EXAMPLE 2

Expression of the Botulinum Toxin Type A-L (BoNt/A-L) Chain Fusion Proteins

Example 2 describes the methods to verify expression of the wild-type L chains, which may serve as a therapeutic component, in bacteria harboring the pCA-L plasmids. Well isolated bacterial colonies harboring either PCAL are used to inoculate L-broth containing 100 µg/ml ampicillin and 2% (w/v) glucose, and grown overnight with shaking at 30° C.

The overnight cultures are diluted 1:10 into fresh L-broth containing 100 μg/ml of ampicillin and incubated for 2 hours. Fusion protein expression is induced by addition of IPTG to a final concentration of 0.1 mM. After an additional 4 hour incubation at 30° C., bacteria are collected by centrifugation at 6,000×g for 10 minutes.

A small-scale SDS-PAGE analysis confirmed the presence of a 90 kDa protein band in samples derived from IPTG-induced bacteria. This $M_r$ is consistent with kDa) and BoNT/A-L chain (~50 kDa) components. Furthermore, when compared with samples isolated from control cultures, the IPTG-induced clones contained substantially larger amounts of the fusion protein.

The presence of the desired fusion proteins in IPTG-induced bacterial extracts is also confirmed by Western blotting using the polyclonal anti-L chain probe described by Cenci di Bello et al., in Eur. J. Biochem. 219:161 (1993). Reactive bands on PVDF membranes (Pharmacia; Milton Keynes, UK) are visualized using an anti-rabbit immunoglobulin conjugated to horseradish peroxidase (Bio-Rad; Hemel Hempstead, UK) and the ECL detection system (Amersham, UK). Western blotting results confirmed the presence of the dominant fusion protein together with several faint bands corresponding to proteins of lower $M_r$ than the fully sized fusion protein. This observation suggested that limited degradation of the fusion protein occurred in the bacteria or during the isolation procedure. Neither the use of 1 mM nor 10 mM benzamidine (Sigma; Poole, UK) during the isolation procedure eliminated this proteolytic breakdown.

The yield of intact fusion protein isolated by the above procedure remained fully adequate for ell procedures described herein. Based on estimates from stained SDS-PAGE gels, the bacterial clones induced with IPTG yielded 5–10 mg of total MBP-wild-type or mutant L chain fusion protein per liter of culture. Thus, the method of producing BoNT/A-L chain fusion proteins disclosed herein is highly efficient, despite any limited proteolysis that did occur.

The MBP-L chain fusion proteins encoded by the pCAL and pCAL-TyrU7 expression plasmids are purified from bacteria by amylose affinity chromatography. Recombinant wild-type or mutant L chains are then separated from the sugar binding domains of the fusion proteins by site-specific cleavage with Factor $X_2$. This cleavage procedure yielded free MBP, free L chains and a small amount of uncleaved fusion protein. While the resulting L chains present in such mixtures have been shown to possess the desired activities, we have also employed an additional purification step. Accordingly, the mixture of cleavage products is applied to a second amylose affinity column that bound both the MBP and uncleaved fusion protein. Free L chains are not retained on the affinity column, and are isolated for use in experiments described below.

EXAMPLE 3

Purification of Fusion Proteins and Isolation of Recombinant BoNT/A-L Chains

Example 3 describes a method to produce and purify wild-type recombinant BoNT/A light chains from bacterial clones. Pellets from 1 liter cultures of bacteria expressing the wild-type BoNT/A-L chain proteins are resuspended in column buffer [10 mM Tris-HCI (pH 8.0), 200 mM NaCI, 1 mM EGTA and 1 mM DTT] containing 1 mM phenylmethanesulfonyl fluoride (PMSF) and 10 mM benzamidine, and lysed by sonication. The lysates are cleared by centrifugation at 15,000×g for 15 minutes at 4° C. Supernatants are applied to an amylose affinity column [2×10 cm, 30 ml resin] (New England BioLabs; Hitchin, UK). Unbound proteins are washed from the resin with column buffer until the eluate is free of nm. The bound MBP-L chain fusion protein is subsequently eluted with column buffer containing 10 mM maltose. Fractions containing the fusion protein are pooled and dialyzed against 20 mM Tris-HCI (pH 8.0) supplemented with 150 mM NaCI, 2 mM, $CaCl_2$ and 1 mM DTT for 72 hours at 4° C.

Fusion proteins may be cleaved with Factor $X_2$ (Promega; Southampton, UK) at an enzyme:substrate ratio of 1:100 while dialyzing against a buffer of 20 mM Tris-HCI (pH 8.0) supplemented with 150 mM NaCI, 2 mM, $CaCl_2$ and 1 mM DTT. Dialysis is carried out for 24 hours at 4° C. The mixture of MBP and either wild-type or mutant L chain that resulted from the cleavage step is loaded onto a 10 ml amylose column equilibrated with column buffer. Aliquots of the flow through fractions are prepared for SDS-PAGE analysis to identify samples containing the L chains. Remaining portions of the flow through fractions are stored at −20° C. Total E. coli extract or the purified proteins are solubilized in SDS sample buffer and subjected to PAGE according to standard procedures. Results of this procedure indicated the recombinant toxin fragment accounted for roughly 90% of the protein content of the sample.

The foregoing results indicate that the approach to creating MBP-L chain fusion proteins described herein could be used to efficiently produce wild-type and mutant recombinant BONT/A-L chains. Further, the results demonstrate that recombinant L chains could be separated from the maltose binding domains of the fusion proteins and purified thereafter.

A sensitive antibody-based assay is developed to compare the enzymatic activities of recombinant L chain products and their native counterparts. The assay employed an antibody having specificity for the intact C-terminal region of SNAP-25 that corresponded to the BoNT/A cleavage site. Western Blotting of the reaction products of BoNT/A cleavage of SNAP-25 indicated an inability of the antibody to bind SNAP-25 sub-fragments. Thus, the antibody reagent employed in the following Example detected only intact SNAP-25. The loss of proteolysis mediated by added BoNT/A light chain or recombinant derivatives thereof.

EXAMPLE 4

Evaluation of the Proteolytic Activities of Recombinant L Chains Against a SNAP-25 Substrate Both native and recombinant BoNT/A-L chains can proteolyze a SNAP-25 substrate. A quantitative assay may be employed to compare the abilities of the wild-type and their recombinant analogs to cleave a SNAP-25 substrate. The substrate utilized for this assay is obtained by preparing a glutathione-S-transferase (GST)-SNAP-25 fusion protein, containing a cleavage site for thrombin, expressed using the pGEX-2T vector and purified by affinity chromatography on glutathione agarose. The SNAP-25 is then cleaved from the fusion protein using thrombin in 50 mM Tris-HCl (pH 7.5) containing 150 mM NaCI and 2.5 mM $CaCl_2$ (Smith et al., Gene 67:31 (1988)) at an enzyme:substrate ratio of 1:100. Uncleaved fusion protein and the cleaved glutathione-binding domain bound to the gel. The recombinant SNAP-25 protein is eluted with the latter buffer and dialyzed against 100 mM HEPES (pH 7.5) for 24 hours at 4° C. The total protein concentration is determined by routine methods.

Rabbit polyclonal antibodies specific for the C-terminal region of SNAP-25 are raised against a synthetic peptide having the amino acid sequence, CANQRATKMLGSG (SEQ ID#7). This peptide corresponded to residues 195 to 206 of the synaptic plasma membrane protein and an N-terminal cysteine residue not found in native SNAP-25. The synthetic peptide is conjugated to bovine serum albumin (BSA) (Sigma; Poole, UK) using maleimidobenzoyl-N-hydroxysuccinimide ester (MBS) as a cross-linking agent (Sigma; Poole, UK) to improve Affinity purification of the anti-peptide antibodies is carried out using a column having the antigenic peptide conjugated via its N-terminal cysteine residue to an aminoalkyl agarose resin (Bio-Rad; Hemel Hempstead, UK), activated with iodoacetic acid using the cross-linker ethyl 3-(3-dimethytpropyl) carbodiimide. After successive washes of the column with a buffer containing 25 mM Tris-HCI (pH 7.4) and 150 mM NaCl, the peptide-specific antibodies are eluted using a solution of 100 mM glycine (pH 2.5) and 200 mM NaCl, and collected in tubes containing 0.2 ml of 1 M Tris-HCI (pH 8.0) neutralizing buffer.

All recombinant preparations containing wild-type L chain are dialyzed overnight at 4° C. into 100 mM HEPES (pH 7.5) containing 0.02% Lubrol and 10 $\mu$M zinc acetate before assessing their enzymatic activities. BoNT/A, previously reduced with 20 mM DTT for 30 minutes at 37° C., as well as these dialyzed samples, are then diluted to different concentrations in the latter HEPES buffer supplemented with 1 mM DTT.

Reaction mixture include 5 $\mu$l recombinant SNAP-25 substrate (8.5 $\mu$M final concentration) and either 20 $\mu$l reduced BoNT/A or recombinant wild-type L chain. All samples are incubated at 37° C. for 1 hour before quenching the reactions with 25 $\mu$l aqueous 2% trifluoroacetic acid (TFA) and 5 mM EDTA (Foran et al., *Biochemistry* 33:15365(1994)). Aliquots of each sample are prepared for SDS-PAGE and Western blotting with the polyclonal SNAP-25 antibody by adding SDS-PAGE sample buffer and boiling. Anti-SNAP-25 antibody reactivity is monitored using an ECL detection system and quantified by densitometric scanning.

Western blotting results indicate clear differences between the proteolytic activities of the purified mutant L chain and either native or recombinant wild-type BoNT/A-L chain. Specifically, recombinant wild-type L chain cleaves the SNAP-25 substrate, though somewhat less efficiently than the reduced BoNT/A native L chain that serves as the positive control in the procedure. Thus, an enzymatically active form of the BoNT/A-L chain is produced by recombinant means and subsequently isolated. Moreover, substitution of a single amino acid in the L chain protein abrogated the ability of the recombinant protein to degrade the synaptic terminal protein.

As a preliminary test of the biological activity of the wild-type recombinant BoNT/A-L chain, the ability of the MBP-L chain fusion protein to diminish $Ca^{2+}$-evoked catecholamine release from digitonin-permeabilized bovine adrenochromaffin cells is examined. Consistently, wild-type recombinant L chain fusion protein, either intact or cleaved with Factor $X_2$ to produce a mixture containing free MBP and recombinant L chain, induced a dose-dependent inhibition of $Ca^{2+}$-stimulated release equivalent to the inhibition caused by native BONT/A. EXAMPLE 5

Reconstitution of Native L Chain, Recombinant Wild-Type L Chain with Purified H Chain Native H and L chains are dissociated from BoNT/A (List Biologicals Inc.; Campbell, USA) with 2 M urea, reduced with 100 mM DTT and then purified according to established chromatographic procedures (Kozaki et al., *Japan J. Med. Sci. Biol.* 34:61 (1981); Maisey et al., *Eur. J. Biochem.* 177:683 (1988)). Purified H chain is combined with an equimolar amount of either native L chain or recombinant wild-type L chain. Reconstitution is carried out by dialyzing the samples against a buffer consisting of 25 mM Tris (pH 8.0), 50 $\mu$M zinc acetate and 150 mM NaCI over 4 days at 4° C. Following dialysis, the association of the recombinant L chain and native H chain to form disulfide-linked 150 kDa dichains is monitored by SDS-PAGE and quantified by densitometric scanning. The proportion of dichain molecules formed with the recombinant L chains is lower than that obtained when native L chain is employed. Indeed, only about 30% of the recombinant wild-type or mutant L chain is reconstituted while >90% of the native L chain reassociated with the H chain. In spite of this lower efficiency of reconstitution, sufficient material incorporating the recombinant L chains is easily produced for use in subsequent functional studies.

EXAMPLE 6

Preparation of Maltose-Binding-Protein-TeTx-L Chain Constructs

This Example describes a method to create recombinant plasmids that encodes maltose-binding fusion proteins of wild-type L chain. *E. coli* K-12 strain TG1 is used as a host for the propagation of all plasmid constructs described below. Plasmid pMAL-L (wild-type L chain gene) is constructed by polymerase chain reaction (PCR) amplification of a 1417-bp fragment encoding. L chain from plasmid pTet87 that has been described by Fairweather et al., in *FEBS Lett.* 323:218 (1993). The two polynucleotide primers, called a and d, that are employed in this PCR amplification has the sequences 5'-AGATGGTCGA CATGCCAATAACCATAAATAAT-3' (SEQ ID#5) and 5'-ACGCGAAGCTTTTATCATGCAGTTCTATTATA-3' (SEQ ID#6), respectively. The amplification product of this reaction is digested with Sall and Hindlll (Promega) and then ligated to vector pMAL-c2 (New England BioLabs) (FIG. 1A) that had been digested with the same enzymes to create the plasmid, pMAL-L, which harbored wild-type TeTx sequences. After purification with the MAGIC DNA CLEAN-UP SYSTEM (Promega), the samples are ligated to pMAL-c2 that has been cleaved with Sail and Hindlll, to create the plasmid, pMAL-LC-Ala2U, which harbors the mutated TeTx sequence.

After subcloning, plasmid DNA is purified from cultures of ampicillin-resistant transformants, and the structures of the constructs is confirmed using restriction mapping and DNA sequencing of the insert. A Sall and Hindlll digest yields a fragment having the expected length of 1417 bp as determine by agarose gel electrophoresis. DNA sequencing confirms that the nucleotide sequence at the junction of the 5'-end of the L chain gene, the multiple cloning site (MCS), the factor X, cleavage site, the L chain and the MBP coding sequences are all in the correct reading frame (FIG. 1A). The availability of the plasmid constructs described above enables the production of recombinant wild-type and mutant L chain fusion proteins. Specifically, cultures of bacterial clones that harbored plasmids pMAL-L are induced with isopropyl-D-thiogalactoside (IPTG) to stimulate high level synthesis of the recombinant fusion proteins. Large-scale purification of the two fusion proteins is accomplished by affinity chromatography of bacterial extracts on amylose affinity resin.

EXAMPLE 7

Expression of TeTx Fusion Proteins and Purification of Wild-Type L Chain Proteins This Example describes the techniques to produce and purify recombinant L chain fusion proteins encoded by the plasmid constructs described in the previous Example B. *E. coli* clones harboring plasmids pMAL-L is grown to densities of roughly $2 \times 10^8$ cells/ml ($A_{500nm} \sim 0.5$) at 37° C. in L-broth that is made 10 g/ml ampicillin and 2 mg/ml glucose. Induction is initiated by the addition of IPTG to a final concentration of 0.3 mM. Cells are harvested 2 hours later by centrifugation at 6000×g for 30 minutes. The resulting pellets are then resuspended in column buffer [10 mM Tris-HCI, 200 mM NaCI, 1 mM ethylene glycol bis(-aminoethyl ether)-N,N,N',N'-tetraacetic acid, and 1 mM dithiothreitol (DTT) (pH 7.4)] containing 1 mM phenylmethanesulfonyl fluoride (PMSF) and lysed by sonication. After centrifugation, crude extracts are applied to an amylose affinity column (2.5×10 cm, 40 ml of resin). Following the removal of nonbound proteins by washing with buffer, the bound MBP-L fusion proteins are eluted with column buffer containing 10 mM maltose according to the procedure descripbed by Mania et al., in Gene 74:365 (1988). The isolated fusion proteins are concentrated to 0.5–1 mg/ml using an Amicon CENTRICON. Protein samples are then analyzed by sodium dodecyl sulfate polyacrylamide gel electrophoresis (SDS-PAGE) and Western blotting, using anti-MBP polyclonal and anti-L chain monoclonal antibodies. SDS-PAGE of both cell extracts indicated the presence of an induced protein band ($M_r \sim 90,000$) that is absent from the coomassie staining pattern of the noninduced cultures. The molecular weight of the protein band is in accordance with that expected from a fusion of MBP and L chain ($M_r \sim 40,000$ and 50,000, respectively). The optimal conditions established for expressing recombinant L chain using the pMAL-c2 vector system are 2 hours of induction with IPTG at 37° C. Neither a longer induction time nor the inclusion of protease inhibitors increased the product yield. Both fusion proteins are soluble in months when stored at −20° C.

After this initial purification step, both MBP-L chain preparations are cleaved at 23° C. for 24 hours with factor X, at an enzymeiprotein ratio of 0.5–1:100 (w/w). This cleavage gave complete conversion of the fusion proteins to the respective wild-type L chain with the liberation of MBP, as confirmed by SDS-PAGE. After extensive dialysis against the column buffer to remove maltose, L chain is further purified by reabsorption onto a new affinity column. The desired product from this purification step is found in the column wash fraction. Fractions of the column wash are monitored for $A_{280nm}$ and checked again by SDS-PAGE and Western blotting.

For amino acid sequencing, recombinant wild-type is run on SDS-PAGE and transferred onto a poly(vinytidene difluoride) membrane as described by Tous et al. in *Anal. Biochem.* 179:50 (1989), with automated Edman degradation performed on a Model 4000 protein sequencer (Chelsea Instruments, London). Microsequencing of the two products revealed four residues identical to those of the N-terminus of native L chain preceded by the 11 amino acids encoded by the multiple cloning site of the vector as depicted in FIG. 1A. Given this success in producing recombinant L chain proteins having the desired structures, we next tested the enzymatic activities of these compositions.

Measurement of the zinc-dependent protease activity of native L chain is employed as an assay for the activity of the recombinant L chain proteins. Two different protein substrates are used in this assay. In the first case, bovine small synaptic vesicles (SSVs) are used. The assay for proteolytic cleavage of the substrate is based on coomassie staining and Western blotting of protein gels.

Methods of assessing the proteolytic activities of the recombinant L chain proteins and quantifying the in vitro activities of native and recombinant L chains are known and may be used to assess and quantify these recombinant L chains.

EXAMPLE 8

Reassociation of TeTx from Native H Chain and Recombinant L Chain

Example 7 describes a method to prepare TeTx dichains that incorporate either native L chain or recombinant wild-type L chain. Native H chain, purified from TeTx as detailed by Weller et al. in *Eur. J. Biochem.* 182:649 (1989), is combined with an equimolar amount of either native L chain or recombinant wild-type L. The mixtures are dialyzed against 2 M urea, 20 mM DTT, 1 M NaCI, and 50 mM Tris-HCI (pH 8.4) with stirring for 18 hours and then further dialyzed without agitation against 50 mM Tris-HCI and 600 mM glycine (pH 8.4) for 72 hours. An aliquot (300 g) is loaded onto an HPLC DEAE column in 25 mM Tris-HCI buffer (pH 8.4) and eluted with an NaCI gradient (0–1 M) in the same buffer. The extent of covalent reconstitution is checked by nonreducing SDS-PAGE and silver staining.

The reassociation of dichain species is confirmed by virtue of the presence of stained high $M_r$ protein bands that comigrated with native TeTx. With respect to recombinant wild-type and mutant L chains, the relative amounts of the dichain species are 55.1 and 56.8%, respectively, as determined by densitometric scanning of the silver-stained gel. Native H chain and L chain gave similar levels of reconstitution. The latter involved interchain disulfide formation as the toxin is converted back to free H chain and L chain upon reduction by DTT.

EXAMPLE 9

Methods of Linking a Therapeutic Component to a Targeting Component

In accordance with the invention, a therapeutic component, such as a light chain, may be attached to a targeting component. The light chain upon which the targeting component is to be attached may be free from other attachments or may already be attached to a translocation component. Many approaches are known for linking chemical compounds to protein chains. For example, a linker molecule may be used to separate the targeting component from the L chain peptide. It is known that 11 amino acids may be attached to the N-terminus of the TeTx-L chain without substantially affecting its functionality. For this reason, the N-terminal portion of either the botulinum toxin or tetanus toxin L chain will be used as the targeting component attachment point.

It is known that most molecules acting as substrates or binding molecules, such as the targeting component, have positions that are not sensitive to steric hindrance. In addition, the linkage process should not introduce chirality into the targeting component. Further, the linker and the targeting component should be attached through a covalent bond. The distance between the L chain and the targeting component may be adjusted by the insertion of spacer components. Preferable spacers have functional groups capable of binding to the linker, drug and L chain and serving to conjugate them. Preferred spacer components include:

1) HOOC—(CH$_2$)$_n$—COOH, where n=1–12, suitable for insertion at the amino terminal end of a peptide, to connect it with a linker on a targeting component.

2) HO—(CH$_2$), —COOH, where n>10, suitable for attachment at the amino terminal of a peptide to connect the L chain with a linker on a targeting component.

3) (C$_5$H$_6$)$_n$, where n>2, suitable for attachment to join the L chain with a linker on the targeting component. The benzene rings provide a rigid spacer between the targeting component and L chain. Of course, appropriate functional groups, for example as identified by X below, will be present on the benzene rings to link the drug and the L chain.

Various linker types are envisioned. For example, in one type the targeting component-linker-L chain molecule remains intact after introduction into cells. In another type, the targeting component-Linker-L chain molecule is metabolized to free the drug after introduction into cells. In yet another type, the component-Linker-L chain molecule is metabolized to free the drug outside the cell surfaces.

Linkers that Remain Intact After Introduction

In one embodiment, a cysteine residue is attached to the end of the L chain molecule by methods well known in the art. For instance, the gene construct that carries the L chain molecule can be mutated to include a cysteine reside at the N-terminal portion of the protein. A maleimide linker is then attached to the Cysteine residue by well known means.

In another embodiment, the linker is attached directly to the targeting moiety. A targeting component-X moiety can have the following groups wherein x may be, (where R$_{30}$ is an alkyl group). Of course, the proper group would not be in an active site or be sterically hindering. The following is an example of one reaction which would link the targeting component-X to the linker molecule.

targeting component-X Br—CH$_2$-Linker→targeting component-X—CH$_2$-Linker

Once the targeting component has a linker attached, the following reaction can be used to link the targeting component to the light chain, for example the light chain of botulinum toxin type A. In this reaction, the light chain, preferably the light chain of botulinum toxin type A, has an accessible lysine group that is used as the attachment point for the targeting component. As discussed hereinabove, an extra amino acid, such as lysine, can be readily added to the N-terminal portion of the L chain gene and used as the attachment point for a targeting component. In the following reaction, sodium cyanoborohydride is used to attach the linker to the lysine group on the L chain molecule.

targeting component-linker-CHO+NaCNBH$_3$+light chain-Lys→ targeting component-linker-CH$_2$—NH-light chain Targeting component that are envisioned for use in the present invention include those that have a free —XH group and that can bind to alpha-2B receptors.

Linkers that Cleave After Introduction

It may be important for the targeting component to be released from the L chain after introduction into the cell. In this method, the targeting component has a free —XH group that is the active site for synthesis with a linker. The —XH group could be an alcohol, phenol, amine, carboxylic acid or thiol group.

The general formula for linking a targeting component to a toxin so that it will be metabolized after introduction is as follows:

targeting component-XH+Linker+Maleimide→targeting component-X-linker-Maleimide+light chain-SH→targeting component-X-linker-Maleimide-light chain, wherein X can be O, N/NH, CO$_2$, S or CONH.

Although the present invention has been described in detail with regard to certain preferred methods, other embodiments, versions, and modifications within the scope of the present invention are possible. For example, an agent according to this invention may be effective in treating any other disorder modulated by alpha-2B adrenergic receptors. Furthermore, while this invention has been described with respect to various specific examples and embodiments, it is to be understood that the invention is not limited thereto and that it can be variously practiced with the scope of the following claims.

What is claimed is:

1. An agent comprising:

a therapeutic component, and a targeting ligand coupled to the therapeutic component, the targeting ligand being effective to bind to the alpha-2B or alpha-2B/alpha-$^2$C adrenergic receptor subtype(s).

2. An agent according to claim 1 wherein the therapeutic component interferes with the release of neurotransmitters from a cell or its processes.

3. An agent according to claim 2 wherein the therapeutic component comprises a light chain component.

4. An agent according to claim 2 wherein the light chain component comprises a light chain or a fragment thereof of a botulinum toxin, a butyricum toxin, a tetani toxin or biologically active variants thereof.

5. An agent according to claim 2 wherein the light chain component comprises a light chain or a fragment thereof of a botulinum toxin type A, B, C1, D, E, F, G or biologically active variants thereof.

6. An agent according to claim 2 wherein the light chain component comprises a light chain or a fragment thereof of a botulinum toxin type A or biologically active variants thereof.

7. An agent according to claim 1 wherein the therapeutic component inactivates cellular ribosomes.

8. An agent according to claim 7 wherein the therapeutic component is saporin.

9. An agent according to claim 1 which further comprises a translocation component.

10. An agent according to claim 9 wherein the translocation component facilitates the transfer of at least a part of the agent into a cytoplasm of the target cell.

11. An agent according to claim 9 wherein the translocation component facilitates the transfer of the therapeutic component into a cytoplasm of the target cell.

12. An agent according to claim 9 wherein the translocation component comprises a heavy chain component.

13. An agent according to claim 12 wherein the heavy chain component comprises a heavy chain or a fragment thereof of a botulinum toxin, a butyricum toxin, a tetani toxin or biologically active variants thereof.

14. An agent according to claim 12 wherein the heavy chain component comprises a heavy chain or a fragment thereof of a botulinum toxin type A, B, C1, D, E, F, G or biologically active variants thereof.

15. An agent according to claim 12 wherein the heavy chain component comprises a heavy chain or a fragment thereof of a botulinum toxin type A or biologically active variants thereof.

16. An agent according to claim 15 wherein the fragment of the heavy chain comprises at least a portion of an amino terminal fragment of the heavy chain.

17. An agent according to claim 9 wherein the therapeutic component comprises a light chain of a botulinum toxin type A and the translocation component comprises a fragment of a heavy chain of a botulinum toxin type A, wherein the fragment of a heavy chain can assist in the translocation of at least the therapeutic component into a cytoplasm of a cell.

18. An agent according to claim 1 wherein the targeting ligand is represented by the formula:

Imiloxan

I

19. An agent according to claim 1 wherein the targeting ligand is a compound represented by the formula:

ARC 239

II

20. An agent according to claim 1 wherein the targeting ligand is a compound represented by the formula Prazosin

III

21. An agent according to claim 1 wherein the targeting ligand is a compound represented by the formula:

IV wherein X' is selected from the group consisting of $R_4$—C=C—$R_5$ and $R_4$—C;

a six membered carbon ring structure is formed when X' is $R_4$—C=C—$R_5$;

a five membered carbon ring is formed when X' is $R_4$—C;

$R_1$, $R_2$, $R_3$, $R_4$ and $R_5$ are each independently selected from the group consisting of F, Cl, Br, I, $OR_6$ and H, wherein $R_6$ is H or an alkyl, including a methyl, an ethyl or a propyl.

22. An agent according to claim 1 wherein the targeting ligand is a compound represented by the formula:

VI

23. An agent according to claim 1 wherein the targeting ligand is represented by the formula

VII wherein the dotted lines represent optional double bonds; R is H or lower alkyl; X is S or C(H)R$_{11}$, wherein R$_{11}$ is H or lower alkyl or R$_{11}$ is absent when X is S or when the bond between X and the ring represented by is a double bond; Y is O, N, S, (C(R$_{11}$)X)$_y$, wherein y is an integer of from 1 to 3, —CH=CH— or —Y$_1$CH$_2$—, wherein Y$_1$ is O, N or S; x is an integer of 1 or 2, wherein x is 1 when R$_{12}$, R$_{13}$, or R$_{14}$ is bound to an unsaturated carbon atom and x is 2 when R$_{12}$, R$_{13}$ or R$_{14}$ is bonded to a saturated carbon atom; R$_{12}$ is H, lower alkyl, halogen, hydroxy, lower alkoxy, lower alkenyl, acyl or lower alkynyl or, when attached to a saturated carbon atom, R$_{12}$ may be oxo; R$_{13}$ and R$_{14}$ are, each, H, lower alkyl, halogen, lower alkenyl, acyl or lower alkynyl, or, when attached to a saturated carbon atom, R$_{12}$ may be oxo; R$_{13}$ and R$_{14}$ are, each, H, lower alkyl, halogen, lower alkenyl, acyl, lower alkynyl, aryl, heteroaryl, or substituted aryl or heteroaryl, wherein said substituent is halogen, lower alkyl, lower alkoxy, lower alkenyl, acyl, lower alkynyl, nitro, cyano, trifluoromethyl, hydroxy, or phenyl or, together, are —(C(R$_2$)x)z-; —Y$_1$(C(R$_2$)x)z'-; —Y$_1$(C(R$_2$)x)y Y$_1$-; —(C(R$_2$)x)-Y$_1$—(C(R$_2$)x)-; —(C(R$_2$)x)- Y$_1$—(C(R$_2$)x)-(C(R$_2$)x)- and —Y$_1$—(C(R$_2$)x)-Y$_1$—(C(R$_2$)x)- wherein z is an integer of from 3 to 5, z' is an integer of from 2 to 4 and x and y are as defined above, and further either end of each of these divalent moieties may attach at either R$_{13}$ or R$_{14}$ to form the condensed ring structure and the ring thus formed may be totally unsaturated, partially unsaturated, or totally saturated provided that a ring carbon has no more than 4 valences, nitrogen no more than three and O and S have no more than two.

24. An agent according to claim 1 wherein the targeting ligand comprises an amino acid component.

25. An agent according to claim 24 wherein the amino acid component is an antibody.

26. An agent according to claim 25 wherein the antibody is raised from an antigen component, the antigen component comprises a second extracellular loop of an alpha-2B receptor.

27. An agent according to claim 26 wherein the second extracellular loop is conjugated to a keyhole limpet hemocyanin.

28. An agent according to claim 24 wherein the amino acid component comprises a variant peptide, a variant polypeptide, a variant protein or a variant protein complex of a wild type peptide, polypeptide, protein or protein complex, respectively.

29. An agent according to claim 24 wherein the amino acid component is a variant polypeptide.

30. An agent according to claim 29 wherein the variant polypeptide is a variant heavy chain.

31. An agent according to claim 1 wherein the therapeutic component and the targeting ligand are attached to each other through a spacer component.

32. An agent according to claim 9 wherein the therapeutic component, the translocation component and the targeting ligand are attached to each other through a spacer component.

33. An agent according to claim 32 wherein the therapeutic component is a light chain of a botulinum toxin type A, the translocation component is a fragment of a heavy chain of a botulinum toxin type A which can facilitate the translocation of at least the light chain into a cytoplasm of a cell, and the targeting component is represented by the formula:

IV wherein X' is selected from the group consisting of R$_4$—C=C—R$_5$ and R$_4$—C;
a six membered carbon ring structure is formed when X' is R$_4$—C=C—R$_5$;
a five membered carbon ring is formed when X' is R$_4$—C;
R$_1$, R$_2$, R$_3$, R$_4$ and R$_5$ are each independently selected from the group consisting of F, Cl, Br, I, OR$_6$ and H, wherein R$_6$ is H or an alkyl, including a methyl, an ethyl or a propyl.

34. An agent according to claim 32 wherein the spacer component comprises a moiety selected from the group consisting of a hydrocarbon, a polypeptide other than an immunoglobulin hinge region, and a proline-containing polypeptide identical or analogous to an immunoglobulin hinge region.

35. An agent according to claim 1 useful for treating chronic pain in a mammal, including a human.

36. An agent according to claim 35 wherein the chronic pain is treated without substantially affecting acute pain sensation or tactile sensation.

37. A method for making an agent for treating pain comprising the step of producing a polypeptide from a gene having codes for at least one component of the agent, wherein the agent comprises a therapeutic component, and a targeting ligand coupled to the therapeutic component, the targeting ligand being effective to bind to the alpha-2B or alpha-2B/alpha-2C adrenergic receptor subtype(s).

38. A method for making an agent according to claim 37 wherein the agent further comprises a translocation component.

39. A method according to claim 38 wherein the therapeutic component comprises a light chain of botulium toxin type A and the translocation component comprises a fragment of a heavy chain which is able to facilitate the transfer of at least the light chain into a cytoplasm of the target cell.

40. A method according to claim 38 wherein the targeting ligand comprises an amino acid component.

41. A method according to claim 40 wherein the amino acid component comprises a variant peptide, a variant polypeptide, a variant protein, or a variant protein complex of a wild type peptide, polypeptide, protein or protein complex, respectively.

42. A method according to claim 41 wherein the variant peptide is a variant heavy chain.

43. The agent of claim 1, wherein the targeting ligand selectively binds to the alpha-2B or alpha-2B/alpha-2C adrenergic receptor subtype(s) as compared to the alpha-2A adrenergic receptor subtype.

44. The agent of claim 37, wherein the targeting ligand of the agent selectively binds to the alpha-2B or alpha-2B/alpha-2C adrenergic receptor subtype(s) as compared to the alpha-2A adrenergic receptor subtype.

45. An agent comprising:

a therapeutic component, and a targeting component coupled to the therapeutic component, the targeting component being represented by the formula:

46. An agent comprising:

a therapeutic component, and a targeting component coupled to the therapeutic component, the targeting component comprising an antibody raised from an antigen component comprising a second extracellular loop, the second extracellular loop comprising an amino acid sequence of KGDQGPQPRGRPQCKLNQE (SEQ ID NO: 1).

* * * * *

SEQUENCE LISTING

<160> NUMBER OF SEQ ID NOS: 7

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: a
      polypeptide fragment of a receptor

<400> SEQUENCE: 1

Lys Gly Asp Gln Gly Pro Gln Pro Arg Gly Arg Pro Gln Cys Lys Leu
 1               5                  10                  15

Asn Gln Glu

```
<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: a spacer
      region

<400> SEQUENCE: 2

Glu Pro Lys Ser Cys Asp Lys Thr His Thr Cys Pro Pro Cys Pro
 1               5                  10                  15

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: a primer

<400> SEQUENCE: 3
aaaggccttt tgttaataaa caa                                              23

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: a primer

<400> SEQUENCE: 4
ggaattctta cttattgtat ccttta                                           26

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: a primer

<400> SEQUENCE: 5
agatggtcga catgccaata accataaata at                                    32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: a primer

<400> SEQUENCE: 6
acgcgaagct tttatcatgc agttctatta ta                                    32

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: peptide
      corresponding to a fragment of a synaptic plasma
      membrane protein

<400> SEQUENCE: 7

Cys Ala Asn Gln Arg Ala Thr Lys Met Leu Gly Ser Gly
 1               5                  10
```